(12) United States Patent
Cox (10) Patent No.: US 10,583,275 B1
(45) Date of Patent: Mar. 10, 2020

(54) PERIPHERALLY INSERTED CENTRAL CATHETER AND ASSEMBLY

(71) Applicant: Julia Cox, Claudville, VA (US)

(72) Inventor: Julia Cox, Claudville, VA (US)

(*) Notice: Subject to any disclaimer, the term of this patent is extended or adjusted under 35 U.S.C. 154(b) by 196 days.

(21) Appl. No.: 15/293,383

(22) Filed: Oct. 14, 2016

Related U.S. Application Data (60) Provisional application No. 62/242,269, filed on Oct. 15, 2015.

(51) Int. Cl.
*A61M 25/04* (2006.01)
*A61M 25/02* (2006.01)
*A61M 39/12* (2006.01)

(52) U.S. Cl.
CPC ............ *A61M 25/04* (2013.01); *A61M 25/02* (2013.01); *A61M 39/12* (2013.01); *A61M 2025/024* (2013.01); *A61M 2025/0206* (2013.01); *A61M 2025/028* (2013.01); *A61M 2025/0246* (2013.01); *A61M 2205/584* (2013.01)

(58) Field of Classification Search
CPC .......... A61M 25/02; A61M 2025/0246; A61M 2025/024; A61M 2025/028; A61M 2205/584; A61M 39/12
See application file for complete search history.

(56) References Cited

U.S. PATENT DOCUMENTS

| | | | |
|---|---|---|---|
| 5,693,032 A * | 12/1997 | Bierman | A61M 25/02 604/174 |
| 5,916,199 A * | 6/1999 | Miles | A61M 25/02 604/174 |
| 2006/0065772 A1* | 3/2006 | Grant | A61M 5/1418 242/388.6 |
| 2016/0375224 A1* | 12/2016 | Gilli | A61M 25/02 604/180 |
| 2018/0021486 A1* | 1/2018 | Atashroo | A61M 27/00 604/540 |

\* cited by examiner

*Primary Examiner* — Nathan R Price
*Assistant Examiner* — Anh Bui
(74) *Attorney, Agent, or Firm* — MacCord Mason PLLC (57) ABSTRACT

Devices, assemblies, and methods for fitting and maintaining medical lines are shown and described. In one embodiment, a fitting system includes a housing having a spool and a removable upper cover to secure medical lines without obstructing flow. Other embodiments include a catheter assembly having a peripherally inserted central catheter and a housing fitting. Certain peripherally inserted central catheters include an inactive anchor. The result is devices and methods to improve medical line fitting, placement, advancement, and stability.

12 Claims, 7 Drawing Sheets

PERIPHERALLY INSERTED CENTRAL CATHETER AND ASSEMBLY

This application claims the benefit of U.S. provisional application No. 62/242,269, filed Oct. 15, 2015, which is incorporated herein by reference in its entirety.

FIELD OF THE TECHNOLOGY

The present disclosure relates generally to medical lines and fittings, and more particularly to improved peripherally inserted central catheter devices, systems, and methods.

BACKGROUND

Medical lines provide advantages in numerous medical applications, including cardiac, prolonged IV antibiotic treatment, nutrition delivery, chemotherapy applications, and the like. A peripherally inserted central catheter (PICC) is one common type of intravenous access to a patient. After positioned in a patient, PICCs typically remain in position for an extended period to provide access and manage patient health.

Inserting the PICC into a patient is sterile procedure that is often a demanding task performed by trained health care providers. In conventional systems, a PICC line is a long, slender flexible tube and is inserted into a central vein, for instance via the upper arm, and is advanced to near the patient's heart to generally obtain intravenous access.

Therefore, Applicant desires devices, systems, and methods for properly inserting a PICC to provide intravenous access, without the drawbacks presented by the traditional systems and methods.

SUMMARY

In accordance with the present disclosure, devices and assemblies are provided for fitting support and inserting medical lines and the like. This disclosure provides improved devices, systems, and methods that are convenient, comfortable, and safe for the end user, particularly when used to assemble, insert, and maintain proper positioning and seating of medical lines.

In one embodiment, a fitting system to secure a medical infusion line comprises a a housing having a rear cover supporting an oval-shaped spool protruding from the housing and adapted to enclose and inhibit movement of a portion of the infusion line without obstructing flow through the infusion line; and a removable upper cover to allow access to the spool in a maintenance position and secure the housing in a semi-fixed position.

In particular examples, the system includes an infusion line. A portion of the infusion line may be secured about the spool. In certain examples, the infusion line is a peripherally inserted central catheter.

In some examples, the housing includes a proximate opening and a distal opening. The removable upper cover may include an entry protrusion and an exit protrusion. The entry protrusion and exit protrusion may mate with the corresponding proximate opening and the distal opening in a semi-fixed position. The proximate opening may include a flexible slit adapted to receive the infusion line. The distal opening may include a flexible slit adapted to receive the infusion line. The spool may include an axial receiving slit. The spool may include a receiving cavity. The cavity may be recessed below an upper plane of the spool and adjacent the spool.

In certain examples, the housing includes a pair of snap enclosures. Further, the system may include a secure cap. The secure cap may be a valved needleless secure cap. The secure cap may include a valve having a pressure end. In addition, the secure cap may include a valve having a neutral pressure end.

Another embodiment of a peripherally inserted central catheter comprises an elongated catheter body having a proximate insertion end; an inactive anchor wall encasing a periphery of the proximate insertion end; and a casing sleeve enclosing the inactive anchor wall.

In particular examples, the inactive anchor wall includes a self-positioning weighted encasing. The self-positioning weighted encasing may ease movement through a patient's vein. Further, the self-positioning weighted encasing may automatically reposition in a superior vena cava vein when seated in an inserted position. The proximate insertion end may include a color indicator tip. The casing sleeve may fully encloses the anchor wall. The elongated catheter body may be transparent. For instance, the transparent catheter body may be a material chosen from polyurethanes, silicones, Teflons, polyethylenes, copolymers, and a combination thereof. In certain examples, the catheter is power injectable.

A further embodiment of a catheter fitting system to secure a peripherally inserted central catheter comprises a housing having a proximate opening, a distal opening, and an oval-shaped spool adapted to enclose and inhibit movement of a portion of the catheter without obstructing flow through the catheter; and a removable upper cover including an entry protrusion and an exit protrusion.

In certain examples, the proximate opening includes a flexible slit to receive the catheter. The distal opening may include a flexible slit adapted to receive the catheter. The spool may include an axial receiving slit. The spool may include a receiving cavity. The cavity may be recessed below an upper plane of the spool and adjacent the spool. The housing may include a pair of snap enclosures.

Another embodiment of a catheter assembly comprises a peripherally inserted central catheter, wherein the catheter including: an elongated catheter body having a proximate insertion end; an inactive self-positioning weighted anchor wall encasing a periphery of the proximate insertion end, and a casing sleeve enclosing the inactive anchor wall; and a housing having a spool adapted to enclose and inhibit movement of a portion of the catheter without obstructing flow through the catheter.

In particular examples, the self-positioning weighted encasing eases movement through a patient's vein. The self-positioning weighted encasing may automatically reposition in a superior vena cava vein when seated in an inserted position. The proximate insertion end may include a color indicator tip. The casing sleeve may fully enclose the anchor wall. The elongated catheter body may be transparent. For instance, the transparent catheter body may be polyurethanes, silicones, Teflons, polyethylenes, copolymers, and a combination thereof.

In certain examples, the housing includes a proximate opening and a distal opening. The assembly may include removable upper cover. The removable upper cover may include an entry protrusion and an exit protrusion. The proximate opening may include a flexible slit adapted to receive the catheter. The distal opening may include a flexible slit adapted to receive the catheter. The spool may include an axial receiving slit. The spool may be an oval-shaped spool and including a receiving cavity. The cavity may be recessed below an upper plane of the spool and adjacent the spool.

In some examples, the housing includes a pair of snap enclosures. In addition, the assembly may include a secure cap. The secure cap may be a valved needleless secure cap. The secure cap may include a valve having a pressure end and a neutral pressure end.

Another alternative embodiment of the disclosure is a catheter assembly having a peripherally inserted central catheter and a secure fitting. Typically, the peripherally inserted central catheter has proximate end with an inactive anchored wall and an elongated distal end. Typically, the secure fitting inhibits movement of a portion of the catheter's distal end.

In some examples, the secure fitting includes a body having a removable front cover and rear cover. The body may have a pair of opposing snap closures to secure the front cover and the rear cover. The body may have a receiving cavity to secure excess length of the catheter. The receiving cavity may have a proximal slit to clamp the catheter. The receiving cavity may have a spool to secure a length of the catheter. The body may have a lip to secure the catheter from becoming unwrapped around the spool. The assembly also includes a secure cap. For instance, the assembly may include a valved needleless secure cap. The secure cap may include a valve having a pressure end. Further, the secure cap may include a valve having a neutral pressure end.

In yet another embodiment, a catheter assembly includes a peripherally inserted central catheter having an elongated catheter body, an inactive self-positioning weighted anchor wall, and casing sleeve, and a secure fitting. Typically, the elongated catheter body has a proximate insertion end. The inactive self-positioning weighted anchor wall may encase a periphery of the proximate insertion. The casing sleeve may enclose the inactive anchor wall. The secure fitting may inhibit movement of a portion of the catheter's distal end.

The above summary was intended to summarize certain embodiments of the present disclosure. Embodiments will be set forth in more detail in the figures and description of embodiments below. It will be apparent, however, that the description of embodiments is not intended to limit the present inventions, the scope of which should be properly determined by the appended claims.

BRIEF DESCRIPTION OF THE DRAWINGS

Embodiments of the disclosure will be better understood by a reading of the Description of Embodiments along with a review of the drawings, in which.

DESCRIPTION OF EMBODIMENTS

In the following description, like reference characters designate like or corresponding parts throughout the several views. Also in the following description, it is to be understood that such terms as "forward," "rearward," "left," "right," "upwardly," "downwardly," and the like are words of convenience and are not to be construed as limiting terms.

Figure 1:
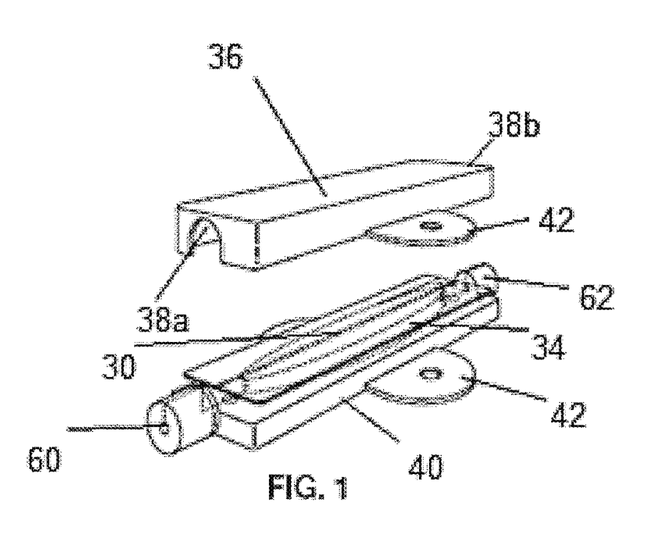
FIG. 1 is a front perspective view of a fitting housing according to an embodiment of the disclosure with elements removed for clarity.
Figure 6A:
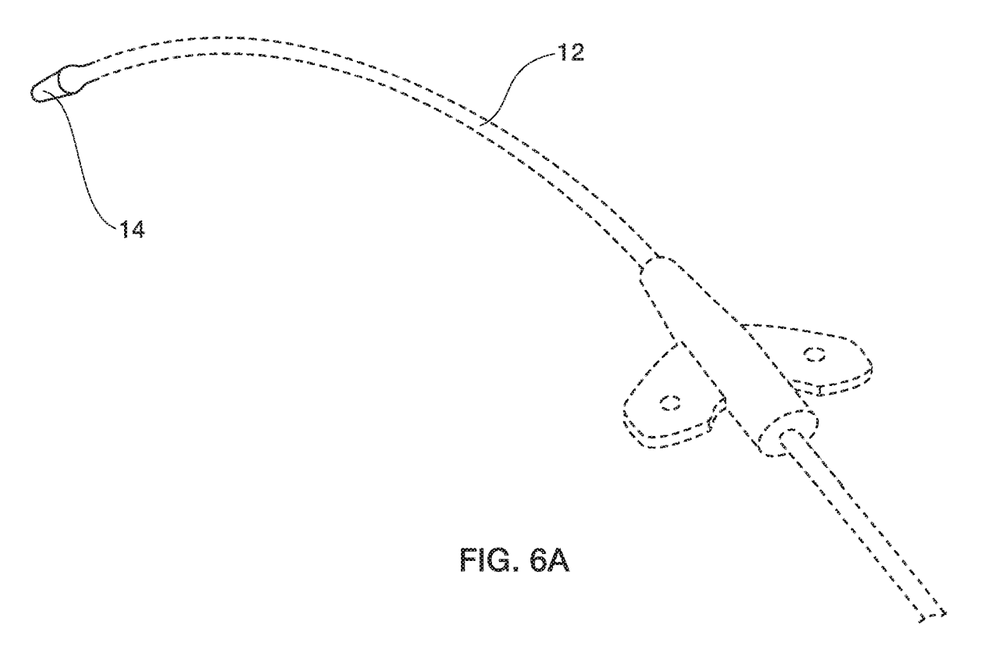
FIG. 6A is a schematic diagram of a catheter according to an embodiment of the disclosure.
Figure 7:
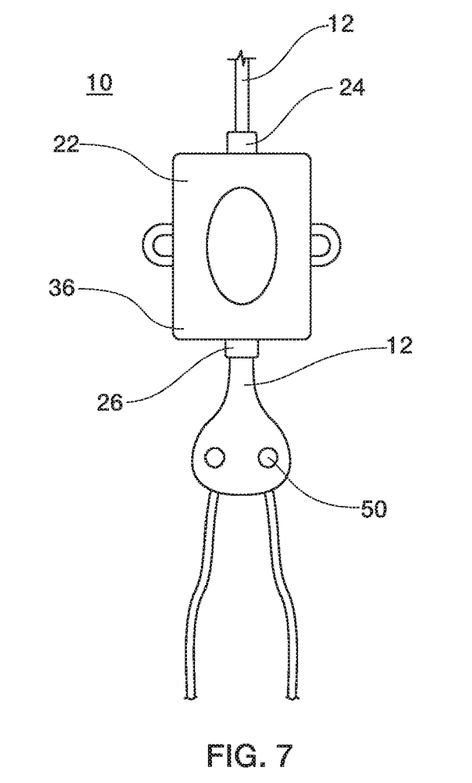
FIG. 7 is a front perspective view of a catheter assembly embodiment.

Referring now to the drawings in general and FIG. 1 in particular, it will be understood that the illustrations are for the purpose of describing embodiments of the disclosure and are not intended to limit the disclosure or any invention thereto. As best seen in FIGS. 1, 6A, and 7, medical line fittings, assemblies, and lines are shown embodied according to the present disclosure.

The medical lines shown and described include any medical, infusion, catheter, or similar lines. The lines comprise a variety of styles, configurations, and sizes that may be placed into a patient for a variety of purposes, including but not limited to a vein in a patient's neck or chest to inject fluids into the central venous circulation. For instance, one example catheter is a peripherally inserted central catheter as recognized by those of ordinary skill in the art having the benefit of this disclosure and described in *The Official Publication of the Infusion Nurses Society* (Volume 37, Number 6, 2014), the teachings of which are incorporated herein.

The fitting systems herein generally position and retain any of the lines shown and described in place to provide and maintain proper intravenous access to the body of the patient. FIG. 1 illustrates one example of a fitting system that is positioned at the upstream insertion site to secure a portion of the line without obstructing flow. As shown, the fitting includes a rear cover 40 that supports a spool 34 to secure a length of the line in a semi-fixed position. In particular examples, the spool 34 is an oval-shaped spool, with tapered edges to minimize obstructing flow during infusion. Applicant has discovered unexpected flow and retention with the oval-shaped spool. Other spools include a variety of other shapes and designs. In addition, the fitting includes a proximate entry opening 60 and an opposing distal exit opening 62. Further, the fitting includes a cavity 30 recessed between the spool 34 and the walls of the rear cover 40. The fitting may also include a closure system, including but not limited to corresponding snap closures 42, to removably secure the elements as shown and described herein.

Figure 2:
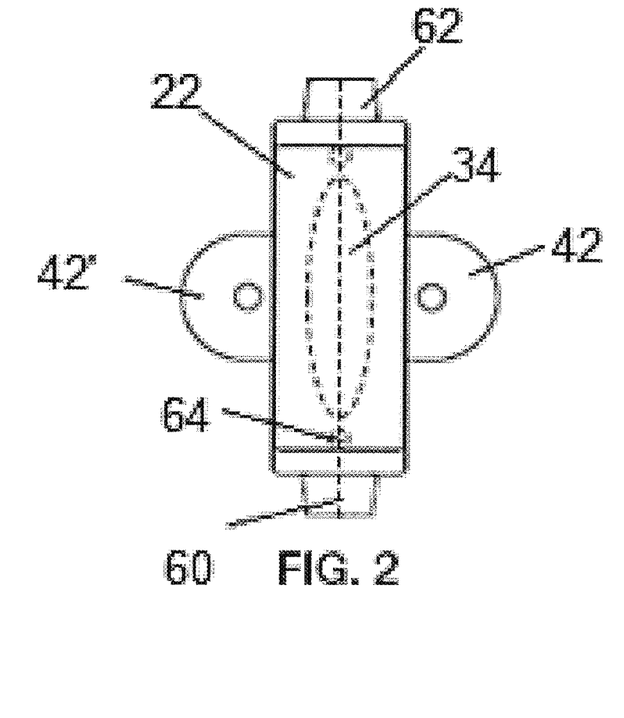
FIG. 2 is a top view of the fitting embodiment introduced in FIG. 1.

As further shown in FIGS. 1 and 2, the fitting may include a removable upper cover 36 to allow access to the spool 34 and/or cavity 30 in a maintenance position and secure the rear and upper elements together in a semi-fixed position. The removable upper cover 36 may include an entry protrusion 38*a* and an exit protrusion 38*b*. In particular examples, the entry protrusion 38*a* and an exit protrusion 38*b* mate with the corresponding proximate entry opening 60 and distal exit opening 62 in a semi-fixed position minimize obstructing flow or the like.

Figure 3:
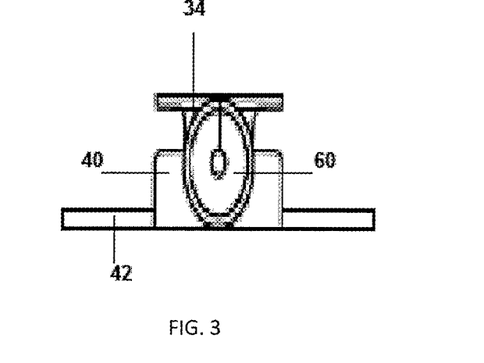
FIG. 3 is an end view of the fitting embodiment shown in FIG. 1.
Figure 4:
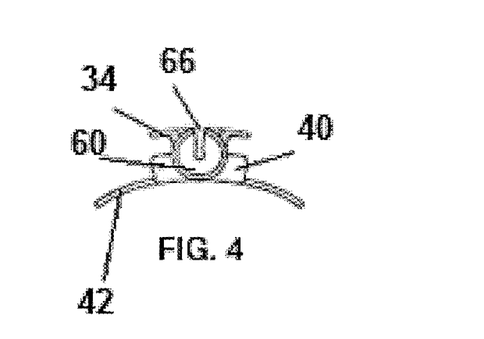
FIG. 4 is another end view of the fitting embodiment shown in FIG. 1 in a semi-flexed open position.

The fitting may be flexible and/or include slits to allow the line to be secured about the fitting. As shown in FIGS. 3 and 4, the proximate opening 60 and distal opening 62 may have a flexible slit 66 to receive and retain the infusion line. Further, the spool 34 may include an axial receiving slit 64 to receive and retain the infusion line.

Figure 5:
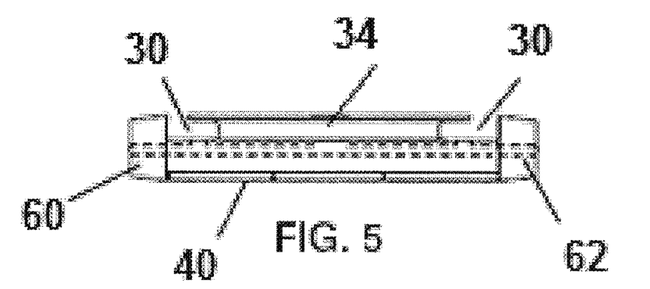
FIG. 5 is a side view of the fitting embodiment shown in FIG. 1.

FIG. 5 shows one example of a receiving cavity 30 of the fitting between the spool and the opposing walls of the fitting housing. For instance, the cavity may be recessed below an upper plane of spool 34, adjacent the spool 34, and within the boundary of the walls of the rear cover housing 40.

Figure 6B:
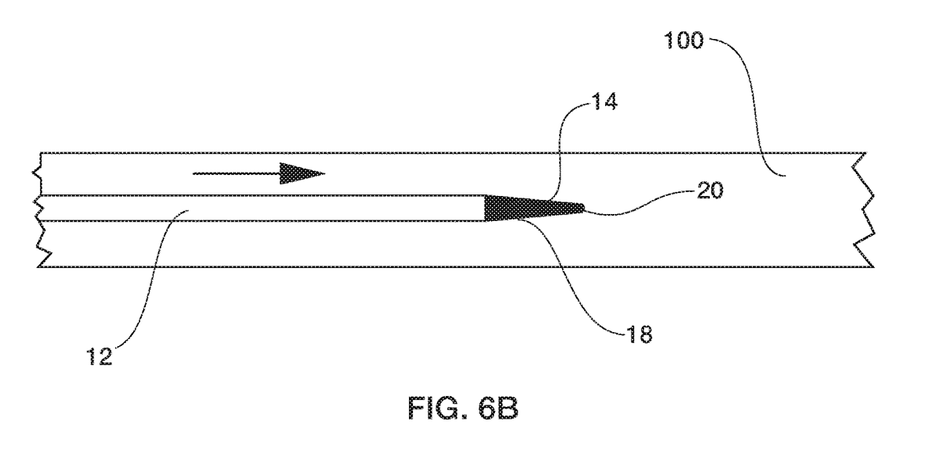
FIG. 6B is a front perspective view of the catheter introduced in FIG. 6A being deployed through a vein according to an embodiment of the disclosure.

Various medical lines are useful in combination with the fittings and assemblies shown and described herein. For example, FIGS. 6A and 6B show embodiments of one particular catheter line have an elongated catheter body 12 and an inactive anchor 14. A casing sleeve 20 generally encloses a weighted anchor wall 14 to prevent point contact of the anchor wall 14 about central venous circulation anatomical features. The catheter is generally deployed in and along a patient's vein 100, for instance without the use of a conventional tip locator, to provide and maintain intravenous access.

FIGS. 6A and 6B show embodiments of a peripherally inserted central catheter having an elongated catheter body 12 with a proximate insertion end and an opposing distal supply end(s) to engage any type of medicine or nutrient as understood by those skilled in the art. In particular examples, the catheter body 12 is transparent. For instance, the catheter body 12 may include any material, including, but not limited to, polyurethanes, silicones, Teflons, polyethylenes, copolymers, combinations thereof, and the like. As shown, the peripherally inserted central catheter generally eases movement through a patient's vein and automatically repositions itself in a vein, for instance within a superior vena cava vein, when seated in an inserted position as generally shown and described herein.

The proximate insertion end of the catheter body 12 generally includes a self-positioning anchor. In one particular example, the weighted anchor wall 14 includes a surgical steel, or the like, weighted end wall with an aperture to deploy any of the fluids generally shown and described herein. The casing sleeve 18 generally encloses the weighted anchor wall 14 to minimize, or eliminate, point contact between the weighted anchor wall 14 and a vein wall. For instance, the casing sleeve 18 may fully enclose the weighted anchor wall 14. The catheter may be power injectable. The catheter may include a color indicator tip 20 to generally indicate a particular medical application as understood by those skilled in the art having the benefit of this disclosure. In particular examples, the sleeve 18, anchor wall 14, or other segment of the elongated body may include a color indicator.

Figure 8A:
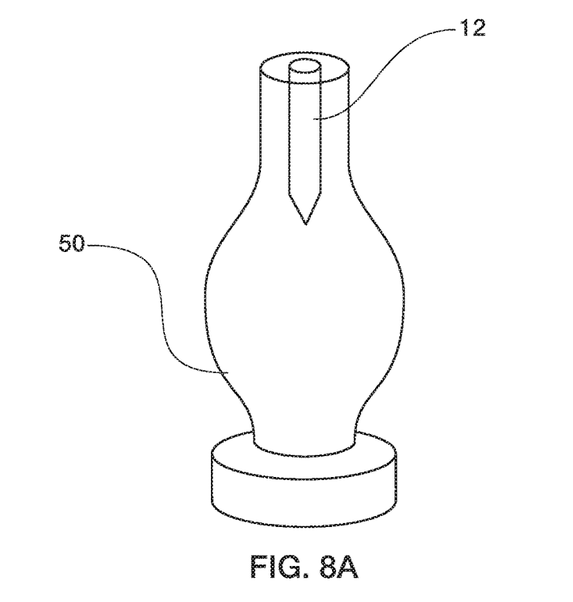
FIG. 8A is a front perspective view of a secure cap embodiment.
Figure 8B:
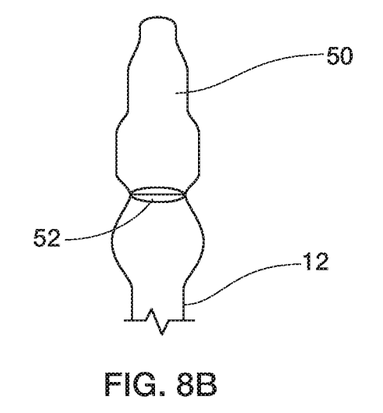
FIG. 8B is a front perspective view of a valve end cap embodiment.
Figure 8C:
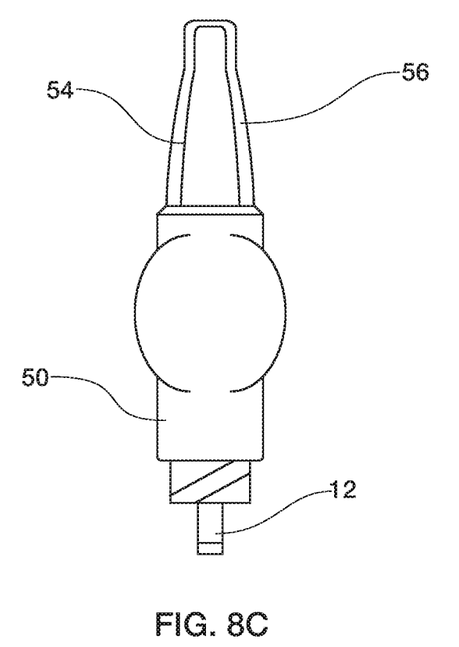
FIG. 8C is a front perspective view of another secure cap embodiment.

FIG. 7 shows an alternative assembly of elements shown and described herein. The assembly may include a secure cap to generally engage the catheter in fluid communication with any of the fluids shown and described herein. For instance, a valved needleless secure cap 50 (as shown in FIGS. 8A-8C) generally secure catheter elements to reduce reflux, for instance reflux initiated from a worn valve. Further, the valved needleless secure cap 50 reduces the opportunity of infection and reduces incidences of bleeding out commonly caused from worn valves. Some examples of the cap 50 are clear, or similarly transparent, to provide visual monitoring of proper flushing and the like. The valved needleless secure cap 50 may include a valve 52. In particular examples, the valve 52 may have a pressure end 54, while the valve may also have a neutral pressure end 56.

In use, any of the catheters shown and described herein may be inserted into a patient's vein and advanced to near the patient's heart to generally obtain intravenous access. For instance, Applicant has unexpectantly discovered the weighted inactive anchored wall 14 allows the catheter to fall into the superior vena cava vein. In an inserted position, the catheter tip shown and described herein removes obscurity concerns presented by conventional systems, and is thus visible on an X-ray or the like. Further, in the event that the catheter moves out of position, Applicant has unexpectantly discovered the weighted inactive anchored wall 14 ensures the catheter self-positions itself back into the superior vena cava vein. Those skilled in the art having the benefit of this disclosure will recognize numerous additional advantages, including reduced medical facility expenses, reduced complications associated with mal-positioned catheters, and minimized patient anxiety associated with inserting and repositioning catheters.

In other embodiments, the disclosure includes a catheter kit. The kit may provide a catheter and/or a fitting attachment to provide and maintain intravenous access to a patient. The kit may comprise a catheter, e.g. any of the catheter segments and weighted anchor elements and examples previously shown or described. Further, the kit may comprise a secure fitting, e.g. any of the fitting body and inner cavity elements and examples previously shown or described. In addition, the kit may comprise a secure cap, e.g. any of the cap and valve elements and examples previously shown or described.

Numerous characteristics and advantages have been set forth in the foregoing description, together with details of structure and function. Many of the novel features are pointed out in the appended examples and claims. The disclosure, however, is illustrative only, and changes may be made in detail, especially in matters of shape, size, and arrangement of parts, within the principle of the disclosure, to the full extent indicated by the broad general meaning of the terms in which the general claims are expressed. It is further noted that, as used in this application, the singular forms "a," "an," and "the" include plural referents unless expressly and unequivocally limited to one referent.

What I claim is:

1. A catheter fitting system to secure a peripherally inserted central catheter, said fitting comprising:
  a unitary housing having a proximate opening comprising a flexible slit adapted to receive said catheter, a distal opening horizontally opposing said proximate opening comprising a flexible slit adapted to receive said catheter, and an oval-shaped spool having a cavity surrounding opposing sides of said spool and adapted to secure and inhibit movement of said catheter within said cavity being wrapped around a front end and a rear end of said spool, and wherein said spool comprising an axial receiving slit adapted to enclose and inhibit movement of a portion of said catheter without obstructing flow through said catheter; and
  a removable upper cover including an entry protrusion and an exit protrusion.

2. The device of claim 1, wherein said cavity being recessed below an upper plane of said spool and adjacent said spool.

3. The device of claim 1, wherein said housing includes a pair of snap enclosures.

4. A fitting system to secure a medical infusion line, said fitting comprising:
  a unitary housing having a proximate opening and a distal opening and a rear cover supporting an oval-shaped spool protruding from said unitary housing and adapted to enclose and inhibit movement of a portion of said infusion line wrapped around opposing sides and a front end and a rear end of said spool without obstructing flow through said infusion line; and a removable upper cover to allow access to said spool in a maintenance position and secure said unitary housing in a semi-fixed position, and wherein said removable upper cover includes an entry protrusion and an exit protrusion, and whereby said entry protrusion and said exit protrusion are adapted to mate with said corresponding proximate opening and said distal opening in a semi-fixed position.

5. The fitting of claim 4, wherein said infusion line being a peripherally inserted central catheter.

6. The fitting of claim 4, wherein said proximate opening includes a flexible slit adapted to receive said infusion line.

7. The fitting of claim 4, wherein said distal opening includes a flexible slit adapted to receive said infusion line.

8. The fitting of claim 4, wherein said spool includes an axial receiving slit.

9. The fitting of claim 4, wherein said spool includes a receiving cavity recessed below an upper plane of said spool and adjacent said spool.

10. The fitting of claim 4, wherein said housing includes a pair of snap enclosures.

11. The fitting of claim 4, further including a valved needleless secure cap.

12. The fitting of claim 11, wherein said secure cap includes a valve having a neutral pressure end.

\* \* \* \* \*